United States Patent [19]

Kihara et al.

[11] Patent Number: 5,166,077
[45] Date of Patent: Nov. 24, 1992

[54] LATEX FOR IMMOBILIZATION OF PHYSIOLOGICALLY ACTIVE SUBSTANCES FOR IMMUNO NEPHELOMETRY

[75] Inventors: Yasuo Kihara; Kenjiro Mori; Tetsuo Watanabe; Takashi Tsuji, all of Osaka, Japan

[73] Assignee: Nitto Denko Corporation, Osaka, Japan

[21] Appl. No.: 540,384

[22] Filed: Jun. 19, 1990

Related U.S. Application Data

[63] Continuation of Ser. No. 188,994, May 2, 1988, abandoned.

[30] Foreign Application Priority Data

Apr. 30, 1987 [JP] Japan ................. 62-108701

[51] Int. Cl.$^5$ .................. G01N 33/546; C12N 11/08; C08F 112/06
[52] U.S. Cl. .................. 436/534; 260/DIG. 45; 435/180; 436/433; 436/909; 524/900; 526/347.1
[58] Field of Search ............... 435/174, 177, 180, 181; 436/533, 534, 909; 260/DIG. 45; 524/900; 526/347.1

[56] References Cited

U.S. PATENT DOCUMENTS

| | | | |
|---|---|---|---|
| 4,140,662 | 2/1979 | Reckel et al. | 436/533 |
| 4,226,747 | 10/1980 | Roncari | 436/534 X |
| 4,264,766 | 4/1981 | Fischer | 436/533 X |
| 4,401,765 | 8/1983 | Craig et al. | 436/533 |
| 4,415,700 | 11/1983 | Batz et al. | 524/548 |
| 4,563,431 | 1/1986 | Pauly et al. | 436/533 |
| 4,735,907 | 4/1988 | Schaeffer et al. | 436/533 X |
| 4,792,527 | 12/1988 | Uchida et al. | 436/533 X |

FOREIGN PATENT DOCUMENTS 0054685 6/1982 European Pat. Off. .
895033 4/1962 United Kingdom .

Primary Examiner—David M. Naff
Attorney, Agent, or Firm—Sughrue, Mion, Zinn, Macpeak & Seas

[57] ABSTRACT

A latex for immobilization of a physiologically active substance is prepared by copolymerizing a monomer mixture comprising:
(a) 100 parts by weight of an aromatic vinyl monome4r;
(b) 0.01 to 5 parts by weight of a vinyl monomer having a sulfonic acid group;
(c) 1 to 20 parts by weight of an α,β-unsaturated carboxylic acid monomer; and
(d) 0.05 to 5 parts by weight of a polyfunctional monomer for internal cross-linking; in water using a water-soluble radical polymerization initiator in the absence of an emulsifying agent. An antigen or antibody or a hapten can be covalently bound to particles of the latex to form a reagent for use in immuno nephelometry.

19 Claims, 1 Drawing Sheet

LATEX FOR IMMOBILIZATION OF PHYSIOLOGICALLY ACTIVE SUBSTANCES FOR IMMUNO NEPHELOMETRY

This is a continuation of application Ser. No. 07/188,994 filed May 2, 1988, now abandoned.

FIELD OF THE INVENTION

The present invention relates to a latex for immobilization of a physiologically active substance, and more particularly, it relates to a latex to immobilize a physiologically active substance by covalently bonding the substance to a latex particle, and a latex reagent prepared using the latex, which is used in the latex immuno nephelometry.

BACKGROUND OF THE INVENTION

An immobilized physiologically active substance obtained by immobilizing a physiologically active substance onto a carrier is used in various applications utilizing its biochemical reaction. Typical examples of such immobilized physiologically active substances are an immobilized enzyme obtained by immobilizing an enzyme onto a water-insoluble carrier, and a reagent for immuno diagnosis as obtained by immobilizing an immunologically active substance. The immobilzed enzyme has been put into practice in the industrial enzymatic reaction in recent years, and the reagent has been widely used in various types of diagnosis.

The enzymatic reaction is commercially employed in the process for production of medicines, foodstuffs and the like. In conventional methods, however, an enzyme is dissolved in an aqueous solution of a substrate and the enzymatic reaction is carried out in the resulting aqueous solution. In accordance with the above methods, however, it is very difficult to feed a fresh enzyme while maintaining predetermined reaction conditions, and to separate the reaction product and the enzyme without inactivation of the enzyme after the enzymatic reaction, and the enzyme is consumed uneconomically. Furthermore, productivity is low because the reaction is carried out batchwise. In order to overcome these problems, an immobilized enzyme as described above has been put into practical use. When a immobilized enzyme is used, the enzymatic reaction is carried out by contacting a substrate with the immobilized enzyme.

As a typical method for preparing such immobilized enzymes, a carrier bonding method is known, comprising bonding an enzyme to a water-insoluble carrier by covalent bonding, ion bonding or physical adsorption. Carriers which have heretofore been used are particles having a particle diameter of 1 mm to several millimeters, for example, derivatives of polysaccharides such as cellulose, dextran, agarose and the like, polyacrylamide, porous glass and the like. An immobilized enzyme obtained by using such particles is usually filled in a column, immobilized and contacted with a substrate solution. Therefore, if the substrate has a high molecular weight, problems arise in that the substrate is difficult to diffuse to the surface of the immobilized enzyme, a long period of time is required in the reaction, and the reaction conversion is low.

It has therefore been proposed to use latex particles as the carrier. For example, a typical latex conventionally used is produced by emulsion polymerizing a sparingly water-soluble radical polymerizable monomer such as styrene in the presence of an emulsifying agent and a water-soluble radical polymerization initiator.

The above emulsifying agent acts to secure polymerization stability during the process of emulsion polymerization and effectively permits to obtain polymer particles having a small particle diameter and a good dispersion stability. Although the reason why the emulsifying agent acts to increase dispersion stability of polymer particles is not necessarily clear, it is generally considered that part of the emulsifying agent is adsorbed onto polymer particles and the remainder is present in a free state in the medium, and that in an aqueous dispersion containing such water dispersion type polymer particles, an adsorption-desorption equilibrium exists between the emulsifying agent adsorbed onto the polymer particles and the free emulsifying agent and, as a result of the equilibrium, stabilization of dispersed polymer particles is attained.

When a latex containing an emulsifying agent is dispersed in a buffer or a physiological saline in order to immobilize a physiologically active substance such as an enzyme onto polymer particles, the above-described adsorption-desorption equilibrium of the emulsifying agent is lost and the dispersion stability of the polymer particles is deteriorated, resulting in aggregation and precipitation of the polymer particles, loss of the degree of freedom of the polymer particles and also a decrease in the biochemical reactivity. The free emulsifying agent often becomes an inhibitor for the biochemical reaction, e.g., the enzymatic reaction.

For this reason, in recent years, a method for preparing a latex by emulsion copolymerizing a monomer having an emulsifying ability by itself, such as sodium styrenesulfonate and polyethylene glycol monomethacrylate, and styrene in the absence of an emulsifying agent has been proposed. In the case of these latex particles, a physiologically active substance must be immobilized by the adsorption method because the latex particles do not have a functional group having a reactivity. This immobilization, however, produces various problems; for example, physiologically active substances which can be immobilized are limited, the pH range in which the immobilized physiologically active substance can be used is limited, and the storage stability is generally poor.

In addition, a method for immobilizing a physiologically active substance by covalently bonding the substance to a carboxylated latex such as a so-called carboxylated polystyrene obtained by copolymerizing styrene and methacrylic acid has been proposed. In general, however, the above conventionally known carboxylated latex has a poor dispersion stability and storage stability. In particular, when a large amount of a physiologically active substance is immobilized using the above latex particles or under the condition that a large amount of a physiologically active substance coexists with the latex particles, the latex particles easily coagulate and precipitate, leading to a serious reduction of the physiological activity. This tendency is marked particularly when the physiologically active substance-immobilized latex is dispersed in a buffer containing an organic solute or physiological saline.

The above-described immunological diagnosis reagent is a reagent for use in immunological diagnosis utilizing the immuno activity that a physiological active substance in the body liquid, such as blood, urine and other liquids to be tested, has. Such immunological diagnosis methods include a method in which an immuno active component is measured by utilizing a specific reaction occurring between an antigen or an antibody and the corresponding antibody or antigen when any one or both of the antigen and the antibody are reacted with a liquid to be tested, such as a body liquid, that is, an aggregation reaction or an aggregation inhibition reaction based on the antigen-antibody reaction. In this method, in order to facilitate the measurement with the naked eye or by an optical method, the antigen or antibody is usually deposited on a water-insoluble fine particle-shaped carrier, such as a latex and erythrocyte, to prepare a diagnosis reagent, and by utilizing the aggregation reaction of such particles, a component to be detected in the body liquid, such as serum, is measured.

The immunological diagnosis reagent is required to have a high sensitivity which, if only a small amount of an immunologically active substance is present in the liquid to be tested, permits to detect the immunologically active substance, and a high specificity which reacts only with the desired immuno active substance. Furthermore, the immunological diagnosis reagent is required to maintain its high detection sensitivity and specificity even when stored for a long period of time.

As such immunological diagnosis reagents, a diagnosis reagent in which polystyrene latex particles are used as the carrier and an antigen or antibody is immobilized on the surface of the particle by physical adsorption; a diagnosis reagent in which an antigen or antibody is immobilized by covalently bonding the antigen or antibody to carboxylated latex particles using carbodiimide, dialdehyde and the like; and so forth have heretofore been proposed. All of these reagents, however, have problems in that dispersion stability and storage stability are poor. Furthermore, when reacted with a liquid to be tested, those reagents sometimes cause the aggregation reaction not only with the corresponding positive substance but also with a negative substance. This aggregation reaction is called a "non-specific aggregation reaction". This non-specific aggregation reaction is a vital defect for the diagnosis reagent.

In recent years, in order to prevent the above non-specific aggregation reaction of latex, there has been developed the latex immuno nephelometry in which a liquid to be detected, such as serum and urine, is diluted to several hundred times to several thousand times the original volume thereof and reacted with a latex in an optical cell, and the latex aggregation reaction based on the antigen-antibody reaction is determined by an absorbance of visible light, near infrared light, ultraviolet light, laser light and the like, or by an optical change in turbidity, scattering and the like.

In this method, however, the dilution of the liquid to be detected to a great extent as described above naturally causes a marked reduction in sensitivity and further increases a deviation in optical change. Therefore, this method is poor in reproductivity of measurement. On the other hand, if the amount of the antigen or antibody, for example, immobilized on the latex is increased in order to increase the sensitivity of the latex reagent, the deviation in optical change is increased and the concentration of antigen or antibody in the liquid to be detected which can be measured is limited. Furthermore, as described above, the non-specific aggregation reaction rather readily occurs.

SUMMARY OF THE INVENTION

The present invention is intended to overcome the above-described problems of the prior latex as a carrier which is used in the preparation of immobilized physiologically active substance.

Accordingly, an object of the present invention is to provide a latex for immobilization of a physiologically active substance, which can be produced by polymerization with high stability and reproductivity in the absence of an emulsifying agent, contains latex particles having a narrow particle diameter distribution, has excellent dispersion stability and storage stability, permits to firmly immobilize a physiologically active substance by covalent bonding, and provides an immobilized physiologically active substance having excellent dispersion stability and storage stability.

Another object of the present invention is to provide a latex reagent for use in the latex immuno nephelometry, which is prepared by covalently bonding an antigen, an antibody or haptene to latex particles, has excellent dispersion and storage stability, and permits to measure the amount of the antigen or antibody in a liquid to be detected, with high accuracy and reproductivity in a wide concentration range of the liquid without causing the non-specific aggregation reaction.

Further object of the present invention is to provide a process for preparing the latex reagent.

DETAILED DESCRIPTION OF THE INVENTION

Figure 1:
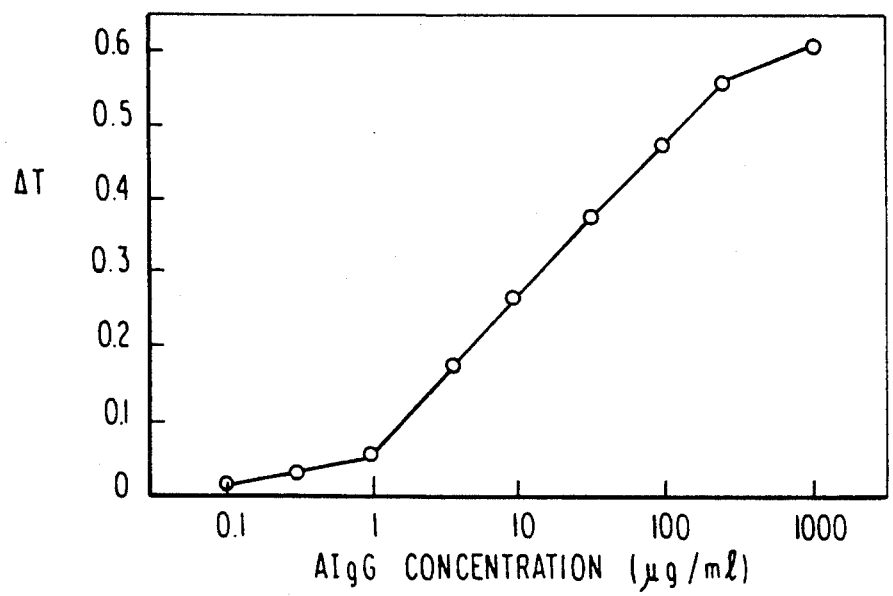
FIG. 1 is a graph showing a relationship between the concentration of an anti-rabbit IgG antibody and a change in absorbance when a latex reagent using the latex particles of the present invention as the carrier is used.

The latex for immobilization of a physiologically active substance according to the present invention comprises copolymer particles having an average particle diameter of 0.03 to 2.0 $\mu$m,, the copolymer particles being obtained by copolymerizing a monomer mixture comprising:

(a) 100 parts by weight of an aromatic vinyl monomer;
(b) 0.01 to 5 parts by weight of a vinyl monomer having a sulfonic acid group;
(c) 1 to 20 parts by weight of an $\alpha,\beta$-unsaturated carboxylic acid monomer; and
(d) 0.05 to 5 parts by weight of a polyfunctional monomer for internal cross-linking;

in water using a water-soluble radical polymerization initiator in the absence of an emulsifying agent.

Further, the latex reagent for latex immuno nephelometry according to the present invention comprises a latex containing copolymer particles having an average particle diameter of 0.03 to 2.0 $\mu$m,, and an antigen, an antibody or haptene immobilized to the latex by covalent bonding, the copolymer particles being prepared by copolymerizing a monomer mixture comprising:

(a) 100 parts by weight of an aromatic vinyl monomer;
(b) 0.01 to 5 parts by weight of a vinyl monomer having a sulfonic acid group;
(c) 1 to 20 parts by weight of an $\alpha,\beta$-unsaturated carboxylic acid monomer; and
(d) 0.05 to 5 parts by weight of a polyfunctional monomer for internal cross-linking; in water using a water-soluble radical polymerization initiator in the absence of an emulsifying agent.

The latex for immobilization of a physiologically active substance according to the present invention will hereinafter be explained in detail.

Representative examples of the aromatic vinyl monomer which can be used in the present invention are styrene, α-methylstyrene, vinlyltoluene and the like. Of these, styrene is preferred.

In the present invention, the aromatic vinyl monomer is used as a major component of the monomer composition. Therefore, the latex particles of the present invention have a specific gravity of about 1.05, which is nearly equal to that of water or a buffer as a dispersant, and the resulting latex has excellent dispersion stability and is free from aggregation and precipitation of particles even if the latex is stored for a long period of time.

Sulfonic acid group-containing vinyl monomers which can be used in the present invention include alkylenesulfonic acid; a sulfoalkyl acrylate represented by the formula

$CH_2=CR^1COOR^2SO_3M$ wherein $R^1$ is a hydrogen atom or a r (preferably $C_1$-$C_3$, hereinafter the same) alkyl group, preferably a hydrogen atom or a methyl group, $R^2$ is an alkylene group having 1 to 6 carbon atoms, preferably an alkylene group having 1 to 3 carbon atoms, and M is a hydrogen atom, an alkali metal or ammonium; styrenesulfonic acid, its derivatives or its alkali metal salts represented by the formula

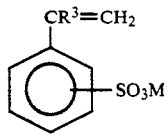

wherein $R^3$ is a hydrogen atom or a lower alkyl group, preferably a hydrogen atom or a methyl group, and M is the same as defined above; 2-acrylamidoalkanesulfonic acid, its derivatives or its alkali metal salts represented by the formula

$CH_2=CR^4CONH-R^5-SO_3M$ wherein $R^4$ is a hydrogen atom or a lower alkyl group, preferably a hydrogen atom or a methyl group, $R^5$ is an alkylene group having 1 to 6 carbon atoms, preferably an alkylene group having 3 to 4 carbon atoms, and M is the same as defined above; and the like.

The representative examples of the alkylenesulfonic acid are ethylenesulfonic acid, etc.

The representative examples of the sulfoalkyl acrylate are sulfopropyl (meth)acrylate, its alkali metal salts, etc.

The representative examples of the styrenesulfonic acid, its derivatives or its alkali metal salts are sodium styrenesulfonate, etc.

The representative examples of the 2-acrylamidoalkanesulfonic acid, its derivatives or its alkali metal salts are 2-acrylamido-2-methylpropanesulfonic acid, etc.

The sulfonic acid group-containing vinyl monomer has an effect of increasing polymerization stability at the time of emulsion polymerization of the above-described aromatic vinyl monomer in the absence of an emulsifying agent and also an effect of increasing the dispersion stability of the resulting latex. In order to efficiently exhibit the above effects, the monomer composition of the present invention contains the sulfonic acid group-containing vinyl monomer in an amount of at least 0.01 part by weight per 100 parts by weight of the above-described aromatic vinyl monomer. However, if the sulfonic acid group-containing vinyl monomer is used excessively, polymerization stability and dispersion stability, particularly storage stability, of the resulting latex are reduced. Thus, the sulfonic acid group-containing vinyl monomer is contained in a range of up to 5 parts by weight per 100 parts by weight of the aromatic vinyl monomer, with the preferred range of 0.03 to 5 parts by weight.

The α,β-unsaturated carboxylic acid which can be used in the present invention is preferably an acid represented by the formula:

$R^6CH=CR^7COOH$ wherein $R^6$ is a hydrogen atom, a lower alkyl group, a carboxyl group as a carbo lower alkoxy group, preferably a hydrogen atom or a methyl group, and $R^7$ is a hydrogen atom or a lower alkyl group, preferably a hydrogen atom or a methyl group, with proviso that when $R^6$ is a hydrogen atom or a lower alkyl group, $R^7$ is a carbo lower alkoxy group.

Preferred examples of such acids are acrylic acid, methacrylic acid, itaconic acid, crotonic acid, maleic acid, fumaric acid, monoalkylmaleic acid, monoalkylfurmaric acid, monoalkylitaconic acid and the like. Of these, acrylic acid, methacrylic acid, itaconic acid and mixtures thereof are preferably used.

These acids are essential to provide a carboxyl group as a functional group which immobilizes a physiologically active substance to latex particles by covalent bonding. At the same time, in the present invention, the acids have an effect of increasing polymerization stability at the time of emulsion polymerization of the monomer mixture and also of increasing the dispersion stability of the resulting latex in an aqueous medium. In order to make an effective amount of a physiologically active substance immobilize on latex particles and at the same time to effectively obtain the above effect, the acids is used in an amount of at least 1 part by weight per 100 parts by weight of the aromatic vinyl monomer. If, however, the acid is used excessively, polymerization stability and dispersion stability of the resulting latex are rather deteriorated. Therefore, the acid is generally used in a range of not more than 20 parts by weight per 100 parts by weight of the aromatic vinyl monomer. The particularly preferred range is from 2 to 100 parts by weight.

In addition, the present invention uses a polyfunctional monomer for internal cross-linking as a monomer component. This polyfunctional monomer for internal cross-linking acts to introduce a cross-linked structure in the resulting copolymer. The polyfunctional monomer inhibits the formation of undesirable water-soluble polymers and at the same time, is effective to render the latex particles non-swelling, thereby increasing the dispersion stability of polymer particles in the aqueous medium.

Poly(meth)acrylates of aliphatic polyhydric alcohol are preferably used as such polyfunctional monomers for internal cross-linking, for example. The representative examples thereof include ethylene glycol dimethacrylate, diethylene glycol dimethacrylate, triethylene glycol dimethacrylate, dipropylene glycol dimethacrylate, 1,3-butylene glycol dimethacrylate, triethylene glycol diacrylate, trimethylolpropane trimethacrylate, trimethylolpropane triacrylate, tetramethylolmethane tetraacrylate and the like. In addition, divinylbenzene, N,N'-methylenebisacrylamide and the like can also be used as the polyfunctional monomer for internal cross-linking.

The polyfunctional mixer for cross-linking is used in an of 0.05 to 5 parts, preferably 0.1 to 3 parts, by we per 100 parts by weight of the above aromatic vinyl monomer. If the amount of the polyfunctional monomer is less than 0.05 part by weight, the cross-linking density in latex particles is too small. On the other hand, if the amount thereof is more than 5 parts by weight, polymerization stability and dispersion stability of the resulting latex are rather undesirably reduced.

In accordance with the present invention, the above monomers are emulsion copolymerized in water using a water-soluble radical polymerization initiator in the absence of an emulsifying agent, whereby a latex having uniform particle diameter and excellent dispersion stability and storage in water can be obtained. Great features of the monomer composition which can be used in the present invention are that copolymerization can be carried out in a stable manner without using an emulsifying agent and the dispersion state of the resulting latex is maintained stably.

In the above emulsion copolymerization, although the concentration of the monomer composition in water varies depending on the average particle diameter of polymer particles in the resulting latex, it is usually in a range of 1 to 60 by weight, preferably 5 to 40% by weight.

As described above, a water-soluble radical polymerization initiator is used as the polymerization initiator. Usually, persulfuric acid salts such as potassium persulfate, sodium persulfate, ammonium persulfate and the like, and redox polymerization initiators comprising the persulfuric acid salts and thiosulfuric acid salts such as sodium thiosulfate, potassium thiosulfate, sodium hydrogenthiosulfate and the like, or sulfurous acid salts such as sodium sulfite, potassium sulfite, sodium hydrogensulfite and the like, are preferably used, although the present invention is not limited thereto. The amount of the polymerization initiator used is preferably in a range of 0.1 to 1% by weight based on the weight of the monomer mixture. Although the atmosphere in which copolymerization is carried out is not particularly limited, an inert gas atmosphere free of oxygen is preferably employed in order to initiate polymerization reaction in a stable manner. Although the polymerization temperature is not particularly limited, it is usually 20° to 100° C. and preferably 40° to 90° C.

In the present invention, the average particle diameter of latex particles is 0.03 to 2.0 μm and preferably 0.05 to 1.0 μm. If the particle diameter is too small, its recovery of latex particles. On the other hand, if the particle diameter is too large, it is difficult to maintain the stable dispersion state of latex particles in water.

There are no special limitations to the physiologically active substance which is immobilized onto the latex of the present invention. Examples of the substance are various enzymes such as an oxidation-reduction enzyme, translocase, a hydrolytic enzyme, lyase, an isomerization enzyme, ligase and the like, a coenzyme, polypeptide, an antigen, an antibody, haptene, hormones and the like.

The physiologically active substance is immobilized onto the latex particles of the present invention by covalent bonding utilizing the carboxyl group which the latex particles have. In this case, the physiologically active substance may be covalently bonded directly to the latex particle, or may be covalently bonded to a spacer group which has been covalently bonded to the latex particle. When the physiologically active substance is immobilized onto the latex particle through the spacer group as in the above latter embodiment, an advantage can be obtained that the degree of freedom of the immobilized physiologically active substance on the latex particle is increased. In the latex particle of the present invention, even if a spacer group is bonded to the latex particle, its dispersion stability and storage stability are not deteriorated.

Compounds which can be used as the above spacer group are bi- or more functional organic compounds. Thus, although polyfunctional polymers are not intended to exclude, bifunctional organic compounds containing a carbon chain group having 1 to 12 carbon atoms are particularly preferred. Representative examples of compounds which can function as the spacer group are diamines such as hexamethylenediamine, dodecamethylenediamine, xylilenediamine and the like, aminoalkylcarboxylic acids such as glycine, β-aminopropionic acid, γ-aminobutyric acid, ε-aminocaproic acid, ε-aminocaprylic acid and the like, amino acids such as lysine, glutamic acid, β-alginine, alycylglycylglysine and the like, and so forth. These compounds are preferably used in the present invention, although the present invention is not limited thereto.

A method for immobilizing a physiologically active substance by covalently bonding it directly to latex particles having a carboxyl group, or by covalently bonding a spacer group to latex particles and then covalently bonding the physiologically active substance to the spacer group is not particularly limited in the present invention, and any desired method conventionally employed can be used.

One of preferred methods is a method in which water-soluble carbodiimide is used as a cross-linking agent. For example, when diamine is used as a spacer group, an amino group of diamine and a carboxyl group of latex particle are reacted to form an amino bond, thereby bonding the spacer group to the polymer particle, and then by using water-soluble carbodiimide in the same manner as above and utilizing the amino group of the spacer group, the physiologically active substance can be immobilized by covalent bonding.

Water-soluble carbodiimides which can be used in the above method include 1-ethyl-3-(3-dimethylaminopropyl)carbodiimide hydrochloric acid salt, 1-cyclohexyl-3-(2-morpholinoethyl)carbociimido-methop-toluene sulfonate, and the like.

In the present invention, depending on the type of the functional group contained in a physioloigcally active substance to be immobilized and the type of above-described bonding reagent, part or all of the carboxyl groups of latex particles may be converted into a functional group other than the carboxyl group, such as an amino group, a hydroxyl group, an aldehyde group and the like, by the use of the spacer group.

When the functional group of the spacer group is an amino group, it is possible that the amino group is activated with dialdehyde and then utilizing the free aldehyde group, the amino group of the physiologically active substance is bonded thereto. Dialdehyde is not particularly limited, and, for example, glutar aldehyde, glyoxal and the like can be used.

The latex reagent for the latex immuno nephelometry of the present invention can be obtained by using the above-described latex particle as a carrier and covalently bonding an antigen, an antibody or haptene to the latex particle.

That is, the latex reagent for the latex immuno nephelometry of the present invention is characterized in that an antigen, an antibody or haptene is immobilized by covalently bonding it to a latex containing copolymer particles having an average particle diameter of 0.03 to 2.0 μm, which are obtained by copolymerizing a monomer mixture comprising:
(a) 100 parts by weight of an aromatic vinyl monomer;
(b) 0.01 to 5 parts by weight of a vinyl monomer containing a sulfonic acid group;
(c) 1 to 20 parts by weight of an α,β-unsaturated carboxylic acid monomer; and
(d) 0.05 to 5 parts by weight of a polyfunctional monomer for internal cross-linking;
in water using a water-soluble radical polymerization initiator in the absence of an emulsifying agent.

The above antigen, antibody or haptene is not particularly limited. For example, IgG, IgM. $C_3$, $C_4$, CRP, F(ab), F(ab)', hormone, polypeptide and the like can be used.

As described above, the latex for immobilization of a physiologically active substance of the present invention is a latex which is prepared by copolymerizing a monomer mixture containing styrene as the main component, and which contains polymer particles having an average particle diameter of 0.03 to 2.0 μm, a specific gravity of about 1.05 and a refractive index of about 1.6. In the production of the latex, polymerization can be carried out with high stability and high reproducivity in the absence of an emulsifying agent. The resulting latex particles have a narrow particle diameter distribution and further have excellent dispersion stability and storage stability. Therefore, a physiologically active substance can be immobilized stably and with high reproductivity by covalent bonding irrespective of the type of the physiologically active substance and the amount of the physiologically active substance immobilized.

Therefore, an immobilized physiologically active substance obtained by covalently bonding a physiologically active substance to the above latex particles as a carrier has also excellent dispersion stability and storage stability.

The latex reagent for the latex immuno nephelometry of the present invention is obtained by immobilizing an antigen, an antibody or haptene to the latex particles having excellent characteristics as described above. Therefore, the latex reagent has excellent dispersion stability and storage stability, and permits to measure the amount of an antibody or an antigen in a liquid to be tested, with high accuracy and high reproducivity without causing the non-specific aggregation reaction and in a wide concentration of the liquid to be tested.

In the case of polymer particles obtained by using a monomer mixture containing methyl methacrylate as the main component, the specific gravity is large and near 1.2, and further the refractive index is int he range of about 1.4 to 1.5. When the refractive index is small, a rate of change in absorbance and turbidity in the latex immuno nephelometry is small and sensitivity is low. On the other hand, according to the present invention, as described above, the latex particles are produced from a monomer mixture containing an aromatic vinyl monomer such as styrene as the main component and, as a result, the polymer particles have a refractive index of about 1.6. Accordingly, this enables the latex particles of the present invention to achieve measurement of high sensitivity in the latex immuno nephelometry.

The present invention is described in greater detail by reference to the following example, although the present invention is not intended to be limited thereto. All parts are by weight, unless otherwise indicated.

EXAMPLE 1

100 parts of styrene, 0.5 part of sodium styrenesulfonate, 5.0 parts of acrylic acid, 0.2 part of triethylene glycol dimethacrylate and 410 parts of distilled water were placed in a reactor, and after sufficiently purging with nitrogen gas, the resulting mixture was heated to 70° C. and stirred at 300 rpm for 30 minutes. An aqueous polymerization initiator solution prepared by dissolving 0.5 part of ammonium persulfate in 20 parts of distilled water was added to the mixture with stirring in the same manner as above, and polymerization was conducted at a temperature of 70° C. for 8 hours. The conversion of polymerization as 98.6%.

Polymer particles of the latex obtained above were measured using a submicron particle analyzer (manufactured by Coaltar Corp.). It was found that the average particle diameter was 0.12 μm and a coefficient of deviation in particle diameter was 8%. The amount of carboxyl group on the surface of the polymer particle was measured by the alkali electroconductivity titration method and found to be 6.2 μmol/m².

In the same manner as above, Latex Nos. 2 to 6 were prepared from the monomer compositions shown in Table 1.

COMPARATIVE EXAMPLE 1

In the same manner as in Example 1, Comparative Latex Nos. 1 to 6 were prepared from the monomer compositions shown in Table 1.

Polymerization stability at the time of emulsion copolymerization and the average particle diameter of latex particles for the latexes of Example 1 and Comparative Example 1 are shown in Table 1.

Each latex was allowed to stand at 40° C. and a pH of 9.0 for 48 hours. A rate of change of the amount of the carboxyl group on the latex particle thus treated is shown as latex stability in Table 1. The rate of change of the amount of the carboxyl group was also measured by the alkali electroconductivity titration method.

TABLE 1

| | Latex No. | Monomer Composition[1] (parts by weight) | | | | | | | |
|---|---|---|---|---|---|---|---|---|---|
| | | Styrene | SSS | SPMA | AMPS | AA | MAA | 3G | DVB |
| Example 1 | 1 | 100 | 0.5 | | | 5.0 | | 0.2 | |
| | 2 | 100 | 2.0 | | | 3.0 | | 2.0 | |
| | 3 | 100 | 0.1 | | | 5.0 | | 2.0 | |

TABLE 1-continued

|  | | | | | | | |
|---|---|---|---|---|---|---|---|
| | 4 | 100 | 0.5 | | | 10 | 1.0 |
| | 5 | 100 | | 0.1 | | 3.0 | 1.0 |
| | 6 | 100 | | | 0.2 | 5.0 | 0.5 |
| Comparative | 1 | 100 | | | | 5.0 | 2.0 |
| Example 1 | 2 | 100 | 0.5 | | | | 1.0 |
| | 3 | 100 | 0.5 | | | 5.0 | |
| | 4 | 100 | 0.1 | | | 25 | 2.0 |
| | 5 | 100 | 10 | | | 3.0 | 2.0 |
| | 6 | 100 | 2.0 | | | 5.0 | 10 |

| | | Properties of Latex | | Properties of Latex Particle | | |
|---|---|---|---|---|---|---|
| | Latex No. | Polymerization Stability[2] | Latex Stability[3] | Particle Diameter (μm) | Refractive Index | Specific Gravity |
| Example 1 | 1 | Stable | less than 3.0% | 0.12 | 1.58 | 1.06 |
| | 2 | Stable | less than 3.0% | 0.18 | 1.59 | 1.06 |
| | 3 | Stable | less than 3.0% | 0.35 | 1.57 | 1.06 |
| | 4 | Stable | less than 3.0% | 0.29 | 1.58 | 1.06 |
| | 5 | Stable | less than 3.0% | 0.24 | 1.59 | 1.06 |
| | 6 | Stable | less than 3.0% | 0.26 | 1.57 | 1.06 |
| Comparative | 1 | Stable | less than 3.0% | 0.42 | 1.57 | 1.06 |
| Example 1 | 2 | Stable | — | 0.26 | — | — |
| | 3 | Stable | +105% | 0.13 | 1.58 | 1.06 |
| | 4 | Aggregation | — | Gelation | — | — |
| | 5 | Aggregation | — | Gelation | — | — |
| | 6 | Aggregation | — | Gelation | — | — |

[1].
SSS = sodium styrenesulfonate,
SPMA = sodium salt of sulfopropyl methacrylate,
AMPS ® = 2-acrylamido-2-methylpropanesulfonic acid,
AA = acrylic acid,
MAA = methacrylic acid,
3G = triethylene glycol dimethacrylate,
DVB = divinylbenzene
[2] In the case of aggregation, 30% or more of aggregated material was formed.
[3] Rate of change in the carboxyl group on the latex particle surface.

Dispersion stability of latex particles in physiological saline and dispersion stability of latex particles to which a spacer group has been bonded are shown in Table 2. Evaluation of the dispersion stability was made by using an optical microscope (×200), and the rating was as follows:

A: Uniform, and no aggregation was observed.
B: No aggregation was observed with the naked eye, but under the microscope, aggregation was observed.
C: Aggregation was observed even with the naked eye.

A method for evaluation of dispersion stability of latex particles in physiological saline, and a method for spacering are shown below.

Stability in Physiological Saline

Latex particles were dispersed in a borate buffer (pH 8.0, 0.01 M) containing 0.9% by weight of sodium chloride, in a concentration of 5%. Just after the dispersion and after two months, dispersion stability was evaluated.

Spacering with m-Xylilenediamine

Latex particles were dispersed in a borate buffer (pH 7.5, 0.01 M) in a concentration of 5% by weight, and 10 ml of the resulting dispersion was mixed with 10 ml of an aqueous m-sylilenediamine solution (0.03 M) and 2 ml of an aqueous 1-ethyl-3-(3-dimethylaminopropyl)-carbodiimide hydrochloric acid salt solution (40 mg/ml). Reaction was conducted at pH 7.5 and a temperature of 10° C. for 24 hours. The reaction mixture was subjected to centrifugal washing with a borate buffer (pH 8.0, 0.01 M) and then again dispersed in the same borate buffer as above in such a manner that the solids content was 5% by weight. Dispersion stability just after the dispersion was evaluated.

Spacering with Cystamine

Latex particles were dispersed in a borate buffer (pH 7.5, 0.01 M) in a concentration of 5% by weight. 10 ml of the resulting dispersion was mixed with 10 ml of an aqueous cystamine solution (0.03 M) and 2 ml of an aqueous 1-ethyl-3-(3-dimethylaminopropyl)carbodiimide hydrochloric acid solution (40 mg/ml). Reaction was conducted at pH 7.5 and a temperature of 10° C. for 24 hours. The reaction mixture was subjected to centrifugal washing with a borate buffer (pH 8.0, 0.01 M) and then again dispersed in the same borate buffer as above in such a manner that the solids content was 5% by weight. The dispersion stability just after dispersion was evaluated.

Thiolation

The disulfide bond of the latex particles which have been subjected to sparing with cystamine was completely reduced with 2-mercaptoethylamine into the thiol group. Dispersion stability just after the reduction was evaluated.

TABLE 2

| | Latex No. | Stability in Physiological Saline | | Stability just after Spacering | | |
|---|---|---|---|---|---|---|
| | | Just after | After 2 Months | m-Xylilenediamine | Cystamine | Thiolation |
| Example 1 | 1 | A | A | A | A | A |
| | 2 | A | A | A | A | A |

TABLE 2-continued

| Latex No. | Stability in Physiological Saline | | Stability just after Spacering | | |
|---|---|---|---|---|---|
| | Just after | After 2 Months | m-Xylilenediamine | Cystamine | Thiolation |
| 3 | A | A | A | A | A |
| 4 | A | A | A | A | A |
| 5 | A | A | A | A | A |
| 6 | A | A | A | A | A |
| Comparative Example 1  1 | A | C | C | C | Not dispersed |
| 2 | A | A | — | — | — |
| 3 | A | B | A | A | B |

Representative examples of an immobilized physiologically active substance with the latex particles of the present invention as the carrier are shown.

Urease Immobilization 3 ml of a borate buffer (pH 7.5, 0.01 M) containing various latex particles shown in Table 1 in a concentration of 5% by weight as m with 1.8 ml of a borate buffer (pH 7.5, 0.01 M), 2.5 ml of an aqueous urease solution (5 mg/ml) and 0.6 ml of an aqueous solution of 1-ethyl-3-(3-dimethylaminopropyl)carbodiimide hydrochloric acid salt, and the resulting mixture was reacted at 4° C. for 24 hours. The reaction mixture was subjected to centrifugal separation and then washed with a borate buffer (pH 7.0, 0.01 M) to obtain a urease-immobilized latex.

Based on a change in absorbance at 280 nm before and after immobilization of urease, the amount of urease immobilized was determined. The activity of urease immobilized per unit weight of latex was divided by the activity of the same amount of free urease, and the quotient was defined as specific activity. The results obtained are shown in Table 3.

In addition, the initial activity of latex particle is shown. The activity of urease was measured by the following method. That is, a 3% by weight aqueous urea solution was used as a substrate and was subjected to an enzymatic reaction at 35° C. The amount of ammonia formed was measured by titrating with 0.2 N hydrochloric acid, and on activity forming 1 mmol of ammonia per one minute was defined as one unit.

The urease-immobilized latex was subjected to centrifugal washing using a borate buffer (pH 7.0, 0.01 M) and then again dispersed in the same borate buffer as above in a concentration of 5% by weight. This washing was repeated ten times. The urease activity of the latex was measured in the same manner as above. This is shown in Table 3 as a relative activity.

TABLE 3

| | Latex No. | Specific Gravity (%) | Initial Activity (Unit/g-particle) | Relative Activity (%) |
|---|---|---|---|---|
| Example 1 | 1 | 59 | 2500 | 94 |
| | 2 | 48 | 2600 | 92 |
| | 3 | 42 | 2600 | 90 |
| | 4 | 55 | 2300 | 93 |
| | 5 | 40 | 2700 | 90 |
| | 6 | 47 | 2650 | 91 |
| Comparative Example 1 | 1* | 44 | 680 | 12 |
| | 2 | 62 | 2800 | 0.0 |
| | 3 | 58 | 2200 | 3.4 |

*Aggregation was caused, and the deviation in value measured was very large.

Immobilization of Rabbit IgG

The latexes spacered with m-xylilenediamine of Latex Nos. 1 to 6 of Example 1 and Comparative Latex Nos. 1 and 3 of Comparative Example 1 were each dispersed in a borate buffer (pH 8.0, 0.01 M) in a solids content of 5% by weight.

3 ml of the above spacered latex, 1.8 ml of a borate buffer (pH 8.0, 0.01 M), 0.6 ml of an aqueous solution of 1-ethyl-3-(3-dimethylaminopropyl)carbodiimide hydrochloric acid salt (5 mg/ml), and 2.1 ml of an aqueous solution of rabbit IgG (5 mg/ml) were mixed and the resulting mixture was reacted at 10° C. for 20 hours. The reaction mixture was subjected to centrifugal washing using the same borate buffer as used above, and dispersed in the same borate buffer in a concentration of 5% by weight.

Thus, a latex reagent in which the rabbit IgG was immobilized in an amount of 40 mg per gram of the latex particle was obtained.

In the case of Comparative Latex of Comparative Example shown in Table 1, the rabbit IgG was immobilized by the adsorption method. The amount of immobilization as 42 mg per gram of the latex particle.

Goat anti-rabbit IgG was dissolved in a borate buffer (pH 8.2, 0.01 M) containing 0.9% by weight of sodium chloride and the resulting solution was used as a liquid to be tested. 50 μl of the solution and 50 μl of the above latex solution were mixed on a glass plate, and aggregation was observed. The results obtained are shown in Table 4.

TABLE 4

| | Latex No. | Concentration of (Goat) Anti-Rabbit IgG Solution (mg/ml) | | | |
|---|---|---|---|---|---|
| | | 1 | 0.1 | 0.01 | 0* |
| Example 1 | 1 | ++ | — | — | — |
| | 2 | ++ | — | — | — |
| | 3 | ++ | ++ | + | — |
| | 4 | ++ | ++ | + | — |
| | 5 | ++ | + | — | — |
| | 6 | ++ | + | — | — |
| Comparative Example 1 | 1 | ++ | ++ | ++ | ++ |
| | 2 | ++ | ++ | ++ | ++ |
| | 3 | ++ | ++ | ++ | — |

*Only the buffer was used.

EXAMPLE 2

Bonding of Spacer Group to Latex Particle

The same monomer mixture as used in Example 1 was emulsion copolymerized in the same manner as in Example 1 in the absence of an emulsifying agent. The latex particles thus obtained were dispersed in a borate buffer (pH 7.5, 0.01 M) in a concentrtiion of 5% by weight. 100 ml of the resulting dispersion was mixed with 100 ml of an aqueous ε-aminocaproic acaid solution (0.03 m) and 20 ml of an aqueous solution of 1-ethyl-3-(3-dimethylaminopropyl)carbodiamide hydrochloric acid salt (38 mg/ml), and the resulting mixture was reacted at 25° C. for 3 hours and then at 4° C. for 17 hours. The reaction mixture was subjected to centrifugal washing with a borate buffer (pH 8.0, 0.01 M) to obtain polymer particles with a spacer group bonded thereto. These polymer particles were again dispersed in the same buffer as above in a solids content of 5% by weight to obtain a spacered latex.

Immobilization of Rabbit IgG 3 ml of the above spacered latex, 1.8 ml of a borate buffer (pH 8.0, 0.01 M), 0.6 ml of an aqueous solution of 1-ethyl-3-(3-dimethylaminopropyl)carbodiimide hydrochloric acid salt (5 mg/ml) and 2.1 ml of an aqueous rabbit IgG solution (5 mg/ml) were mixed and the resulting mixture was reacted at 10° C. for 20 hours. The reaction mixture was subjected to centrifugal washing with the same borate buffer as above and then dispersed in the same borate buffer as above in a concentration of 5% by weight.

The latex was dispersed in a borate buffer (pH 8.0, 0.01 M) containing 0.2% of Bovine serum albumin and 0.9% of sodium chloride to obtain a latex reagent in which the rabbit IgG was immobilized in an amount of 43 mg per gram of the latex particle.

Measurement of Activity of Latex Reagent

Anti-rabbit IgG serum was dissolved in a Bovine serum albumin borate buffer (Bovine serum albumin 0.2%, sodium chloride 0.9%, pH 8.0, 0.01 M) to prepare $\overline{A}IgG$.

30 μl of the above rabbit IgG-imobilized latex reagent and 450 μl of the above Bovine serum albumin borate buffer were placed in a cell, and 150 μl of the above $\overline{A}IgG$ solution was then introduced therein. The resulting mixture was std for 20 seconds and set on a spectral photometer. Absorbance $T_O$ at 600 nm after 30 seconds and absorbance $T_I$ at 600 nm after 100 seconds were measured.

A relationship between absorbance change $\Delta T = T_I - T_O$ and the concentration of the $\overline{A}IgG$ solution is shown in FIG. 1.

When the latex of the present invention is used, a straight line relationship between the concentration of $\overline{A}IgG$ solution and the absorbance change over a wide concentration range of the $\overline{A}IgG$ solution can be obtained.

When in place of the anti-rabbit IgG serum, rheumatism positive and negative serums (not diluted) were used, $\Delta T$ was 0 in the case of negative serum, and $\Delta T$ was 0.104 in the case of positive serum.

$\overline{A}IgG$ did not change at all even after the latex reagent was allowed to stand at room temperature for 6 months.

COMPARATIVE EXAMPLE 2

A carboxylated polystyrene latex having an average particle diameter of 0.18 μm was prepared in the same manner as in Example 1 with the exception that sodium styrenesulfonate was not used as a monomer component.

To this latex was bonded ε-aminocaproic acid as a spacer group in the same manner as above, and IgG was then immobilized thereto.

This IgG immobilized latex was used as a latex reagent, and its activity was measured in the same manner as in Example 2, using rheumatism positive and negative serums (not diluted). In the case of negative serum, $\Delta T$ was 0.180, and in the case of positive serum, $\Delta T$ was 0.171. That is, non-specific aggregation was marked.

Figure 2:
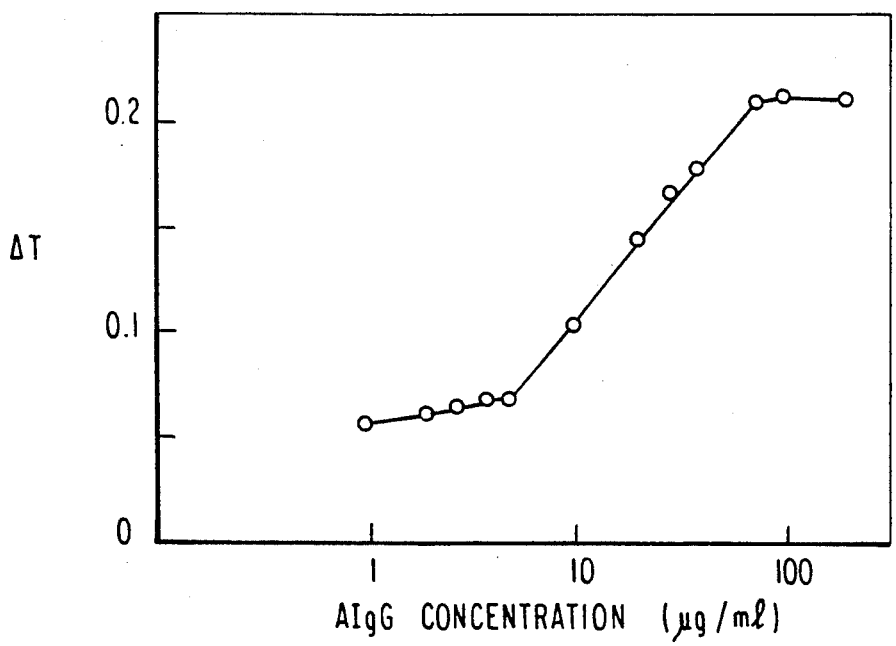
FIG. 2 is a graph showing a relationship between the concentration of the same antibody as above and a change in absorbance when a comparative reagent using a comparative carrier is used.

In the case of the $\overline{A}IgG$ solution, as shown in FIG. 2, the straight line relationship was observed only in the concentration range of 5 to 70 μg/ml.

COMPARATIVE EXAMPLE 3

A carboxylated polystyrene latex having an average particle diameter of 0.14 μm was prepared in the same manner as in Example 1 with the exception that triethylene glycol dimethacrylate was not used as a monomer component.

To this latex was bonded ε-aminocaproic acid as a spacer group in the same manner as in Example 2, and rabbit IgG was then immobilized thereto to obtain a rabbit IgG-immobilized latex reagent.

The $\overline{A}IgG$ activity of the rabbit IgG-immobilized latex was measured just after its preparation and after 6 months in the same manner as in Example 2. The change in $\Delta T$ was marked, and T after 6 months dropped to about 1/10 that just after the preparation.

EXAMPLE 3

A carboxylated polystyrene latex having an average particle diameter of 0.21 μm, was prepared in the same manner as in Example 1 with the exception that as the monomer component, sulfopropyl methacrylate was used in place of the sodium styrenesulfonate.

To this latex was bonded ε-aminocaproic acid as a spacer group in the same manner as above. In place of the rabbit IgG, rabbit anti-human chorionic gonadotropin antibody (hcG) was immobilized in the same manner as above to obtain an anti hcG-immobilized latex reagent.

Using the standard hcG solution, $\Delta T$ was measured in the same manner as above. The results obtained are shown in Table 5.

TABLE 5

| Concentration of Standard hcG Solution (IU/ml) | $\Delta T$ |
|---|---|
| 0.1 | 0.049 |
| 0.3 | 0.140 |
| 0.5 | 0.234 |
| 0.7 | 0.330 |
| 1.0 | 0.472 |
| 1.3 | 0.598 |

While the invention has been described in detail and with reference to specific embodiments thereof, it will be apparent to one skilled in the art that various changes and modifications can be made therein without departing from the spirit and scope thereof.

What is claimed is:

1. A latex for immobilization of a physiologically active substance comprising copolymer particles having an average particle diameter of 0.03 to 2.0 microns, said particles being prepared by copolymerizing in water using a water soluble radical polymerization initiator a monomer mixture consisting essentially of:
   (a) 100 parts by weight of an aromatic vinyl monomer;
   (b) 0.01 to 5 parts by weight of a vinyl monomer having a sulfonic acid group;
   (c) 1 to 20 parts by weight of an α,β-unsaturated carboxylic acid monomer; and
   (d) 0.05 to 5 parts by weight of a polyfunctional monomer for internal crosslinking.

2. The latex as claimed in claim 1, wherein the average particle diameter of the copolymer particles is 0.05 to 1.0 μm.

3. The latex as claimed in claim 1, wherein the aromatic vinyl monomer is styrene, α-methylstyrene or vinyltoluene.

4. The latex as claimed in claim 1, wherein the vinyl monomer having a sulfonic acid group is an alkylene sulfonic acid, a sulfoalkyl acrylate, styrene sulfonic acid, or 2-acrylamidoalkanesulfonic acid.

5. The latex as claimed in claim 1, wherein the amount of the vinyl monomer having a sulfonic acid group is 0.03 to 3 parts by weight.

6. The latex as claimed in claim 1, wherein the α,β-unsaturated carboxylic acid is an acid represented by the formula $$R^6CH=CR^7COOH$$

wherein $R^6$ is a hydrogen atom, a lower alkyl group, a carboxyl group or a carbo lower alkoxy group, and $R^7$ is a hydrogen atom or a lower alkyl group, with proviso that when $R^6$ is a hydrogen atom or a lower alkyl group, $R^7$ is a carbo lower alkoxy group.

7. The latex as claimed in claim 6, wherein the acrylic acid is acrylic acid, methacrylic acid, itaconic acid, crotonic acid, maleic acid, fumaric acid, monoalkylmaleic acid, monoalkylfumaric acid, or monoalkylitaconic acid.

8. The latex as claimed in claim 1, wherein the amount of the α,β-unsaturated carboxylic acid is 2 to 10 parts by weight.

9. The latex as claimed in claim 1, wherein the polyfunctional monomer is a poly(meth)acrylate of aliphatic polyhydric alcohol.

10. The latex as claimed in claim 9, wherein the poly(meth)acrylate of aliphatic polyhydric alcohol is ethylene glycol dimethacrylate, diethylene glycol dimethacrylate, triethylene glycol dimethacrylate, dipropylene glycol dimethacrylate, 1,3-butylene glycol dimethacrylate, triethylene glycol diacrylate, trimethylolpropane trimethacrylate, trimethylolpropane triacrylate or tetramethylolmethane tetraacrylate.

11. The latex as claimed in claim 1, wherein the amount of the polyfunctional monomer is 0.1 to 3 parts by weight.

12. The latex as claimed in claim 1, wherein the concentration of the monomer mixture in water in the copolymerization is 1 to 60% by weight.

13. The latex as claimed in claim 1, wherein the copolymerization is conducted under an inert gas atmosphere.

14. The latex as claimed in claim 1, wherein the copolymerization is conducted at a temperature of 20° to 100° C.

15. The latex as claimed in claim 1, wherein the vinyl monomer having a sulfonic acid group is
   (a) a derivative of styrene sulfonic acid represented by formula (I)
      wherein $R^3$ is a hydrogen atom or a lower alkyl group and M is a hydrogen atom, an alkali metal or ammonium; or
   (b) a derivative of 2-acrylamidoalkanesulfonic acid represented by formula (II)

$$CH_2=CR^4CON-R^5-SO_3M \qquad (II)$$

wherein $R^4$ is a hydrogen atom or a lower alkyl group, $R^5$ is an alkylene group having 1 to 6 carbon atoms, and M is the same as defined above.

16. The latex claimed in claim 15 wherein $R^3$ is formula (I) is a lower alkyl group which is a methyl group.

17. The latex as claimed in claim 15, wherein $R^4$ in formula (II) is a lower alkyl group which is a methyl group.

18. The latex as claimed in claim 15, wherein $R^5$ in formula (II) has 3 to 4 carbon atoms.

19. A latex reagent for latex immuno nephelometry, comprising a latex containing copolymer particles having an average particle diameter of 0.03 to 2.0 μm, and an antigen, an antibody or haptene covalently bound to said latex, said copolymer particles prepared by copolymerizing in water using a water soluble radical polymerization initiator a monomer mixture consisting essentially of:
   (a) 100 parts by weight of an aromatic vinyl monomer;
   (b) 0.01 to 5 parts by weight of a vinyl monomer having a sulfonic acid group;
   (c) 1 to 20 parts by weight of an α,β-unsaturated carboxylic acid monomer; and
   (d) 0.05 to 5 parts by weight of a polyfunctional monomer for internal crosslinking.

* * * * *